United States Patent
Melsheimer

(10) Patent No.: US 8,764,712 B2
(45) Date of Patent: Jul. 1, 2014

(54) MICRO-NEEDLE ARRAY AND METHOD OF USE THEREOF

(75) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 729 days.

(21) Appl. No.: 12/535,314

(22) Filed: Aug. 4, 2009

(65) Prior Publication Data

US 2011/0034860 A1    Feb. 10, 2011

(51) Int. Cl.
*A61M 5/00*    (2006.01)

(52) U.S. Cl.
USPC .............................. 604/173; 604/22

(58) Field of Classification Search
USPC ............. 604/103.01, 103.02, 103.08, 173, 22
See application file for complete search history.

(56) References Cited

U.S. PATENT DOCUMENTS

| | | | |
|---|---|---|---|
| 5,112,305 A | 5/1992 | Barath et al. | |
| 5,681,281 A | 10/1997 | Vigil et al. | |
| 6,083,196 A | 7/2000 | Trautman et al. | |
| 6,197,013 B1 | 3/2001 | Reed et al. | |
| 6,302,870 B1 | 10/2001 | Jacobsen et al. | |
| 6,547,803 B2 | 4/2003 | Seward et al. | |
| 6,638,246 B1 | 10/2003 | Naimark et al. | |
| 6,808,518 B2 | 10/2004 | Wellman et al. | |
| 6,991,617 B2 * | 1/2006 | Hektner et al. | 604/103.01 |
| 7,273,474 B2 | 9/2007 | Chang et al. | |
| 7,465,298 B2 | 12/2008 | Seward et al. | |
| 2002/0045859 A1 | 4/2002 | Gartstein et al. | |
| 2004/0098014 A1 | 5/2004 | Flugelman et al. | |
| 2005/0220836 A1 | 10/2005 | Falotico et al. | |
| 2006/0184092 A1 | 8/2006 | Atanasoska et al. | |
| 2007/0078414 A1 * | 4/2007 | McAllister et al. | 604/272 |
| 2007/0191766 A1 | 8/2007 | McMorrow | |
| 2008/0125743 A1 | 5/2008 | Yuzhakov | |
| 2008/0200883 A1 | 8/2008 | Tomono | |
| 2008/0294116 A1 * | 11/2008 | Wolter et al. | 604/173 |
| 2008/0300610 A1 | 12/2008 | Chambers | |

FOREIGN PATENT DOCUMENTS

| WO | WO2006/116281 A2 | 11/2006 |
|---|---|---|
| WO | WO2007/019539 A2 | 2/2007 |
| WO | WO2007/127808 A2 | 11/2007 |

OTHER PUBLICATIONS

International Search Report and Written Opinion of the International Searching Authority dated Nov. 5, 2010 for corresponding PCT Application No. PCT/US2010/043011.

* cited by examiner

*Primary Examiner* — Kevin C Sirmons
*Assistant Examiner* — Deanna K Hall
(74) *Attorney, Agent, or Firm* — Brinks Gilson & Lione

(57) ABSTRACT

A micro-needle array is provided that may be used to deliver a bioactive agent to a therapeutic target. The micro-needle array preferably includes a substrate, a plurality of micro-needles integral with the substrate, and a bioactive agent. At least one micro-needle preferably includes a top surface, a bottom surface, a side surface, and a cavity defined by an inner surface. The bioactive agent may be disposed on the substrate and the plurality of micro-needles. The at least one micro-needle may further include a slit connecting the cavity to an aperture, the slit extending from the top surface to the bottom surface.

11 Claims, 10 Drawing Sheets

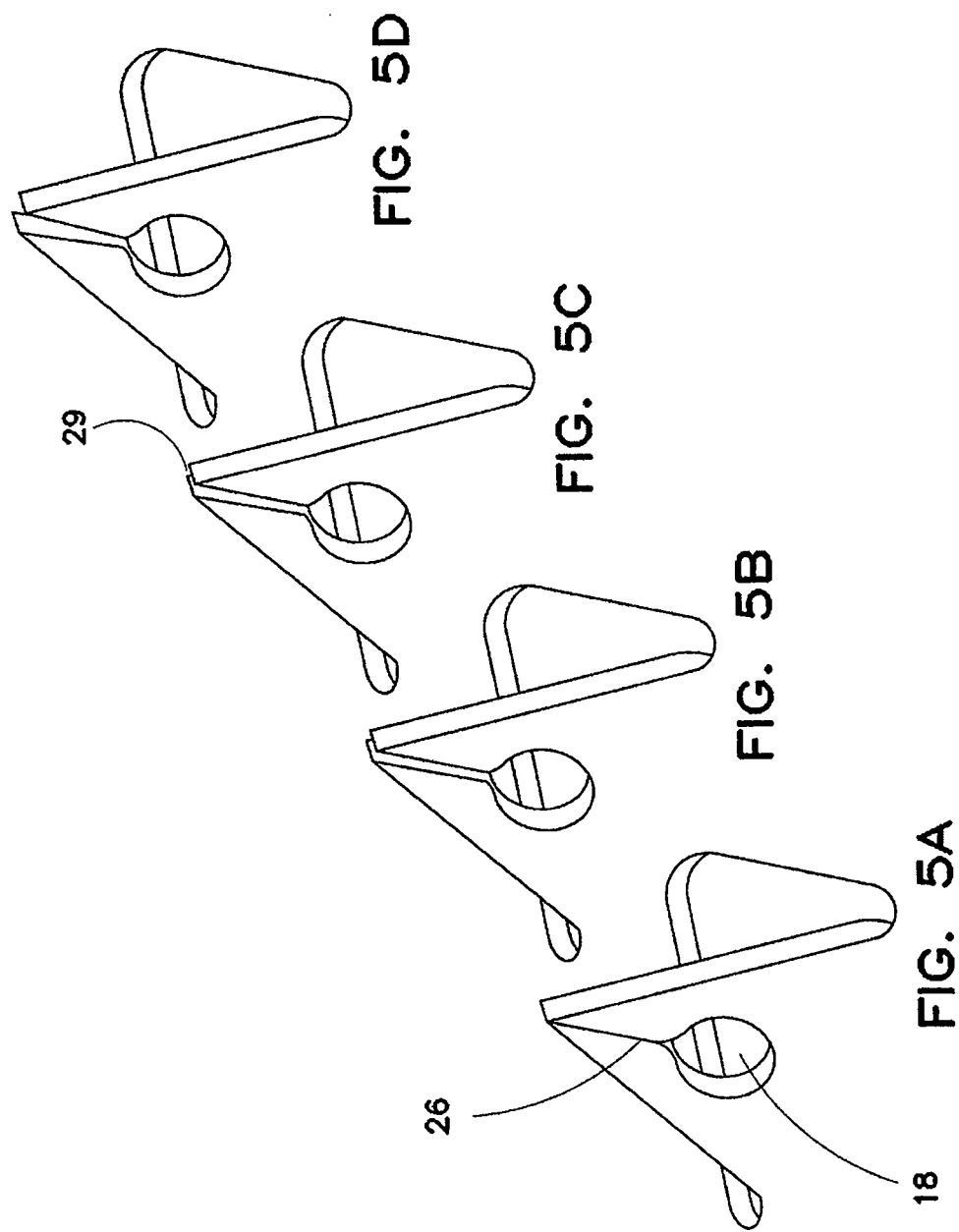

MICRO-NEEDLE ARRAY AND METHOD OF USE THEREOF

TECHNICAL FIELD

The present disclosure relates generally to medical devices, and more particularly to a micro-needle array for delivering a bioactive agent to a therapeutic target.

BACKGROUND

Bioactive agents released from a medical device can be used to treat or mitigate a variety of conditions. An angioplasty balloon, for example, may be configured to release one or more antiproliferative agents, such as paclitaxel, in order to prevent or reduce the incidence of restenonsis. Restenosis refers to the renarrowing of the vascular lumen following vascular intervention. In another example, a prosthetic valve may be configured to deliver an antithrombotic agent, such as heparin, in order to inhibit thrombus formation at the site of implantation. Other combinations of medical devices and bioactive agents may be used to treat a variety of other conditions.

These drug eluting devices are typically configured to deliver the bioactive agent directly to an exposed, exterior surface of the therapeutic target. A paclitaxel coated angioplasty balloon, for example, may be delivered to a site of vascular treatment and thereafter inflated so that the exterior of the balloon contacts the vessel wall. The paclitaxel may then diffuse into the vessel wall from the balloon exterior surface. In some instances, however, delivery of a therapeutically effective amount of bioactive agent can be hindered by the movement of body fluid through or past the implanted device. Specifically, body fluid can wash away or dilute the bioactive agent, preventing effective delivery.

What is needed are devices and methods for facilitating effective delivery of one or more bioactive agents to selected therapeutic targets. In particular, devices are needed that can facilitate drug uptake and diffusion into the therapeutic target.

SUMMARY

The present disclosure generally provides devices and methods for delivery of one or more bioactive agents to a therapeutic target. In one aspect, the present disclosure provides a micro-needle array having a plurality of micro-needles. The micro-needles are configured to contact, and preferably penetrate a therapeutic target, delivering bioactive agent thereto.

In one embodiment, the micro-needle array includes a substrate, a plurality of micro-needles integral with the substrate, and a bioactive agent. At least one of the plurality of micro-needles includes a body including a top surface, a bottom surface, a side surface, and a cavity within the body and defined by an inner surface. The side surface extends from the top surface to the bottom surface. The cavity extends from the top surface to the bottom surface. The bioactive agent is disposed on the micro-needle array, preferably on the substrate and the plurality of micro-needles. The at least one micro-needle may further include a slit connecting the cavity to an aperture. The slit extends from the top surface to the bottom surface. The aperture is located on the side surface.

In another embodiment, the micro-needle array includes a plurality of micro-needles with at least one micro-needle comprising a cavity defined by an inner surface. The cavity extends from a first surface to a second surface. The at least one micro-needle may further include a slit extending from the cavity to an aperture. The slit extends from the first surface to the second surface. A bioactive agent may be disposed on the micro-needle array.

In another aspect, the present disclosure provides a method for delivering a bioactive agent to a therapeutic target. In one embodiment, the method includes positioning an expandable balloon at a therapeutic target, wherein a micro-needle array overlays an outer surface of the balloon. The micro-needle array includes a substrate, a plurality of micro-needles integral with the substrate, and a bioactive agent. At least one of the plurality of micro-needles includes a body including a top surface, a bottom surface, a side surface, and a cavity within the body and defined by an inner surface. The side surface extends from the top surface to the bottom surface. The cavity extends from the top surface to the bottom surface. The bioactive agent is disposed on the micro-needle array, preferably on the substrate and the plurality of micro-needles. The method further includes expanding the balloon to cause the micro-needles to contact the therapeutic target. The contact is maintained with the therapeutic target for a time sufficient to deliver a therapeutically effective amount of bioactive agent to the therapeutic target.

Other systems, methods, features and advantages will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The system may be better understood with reference to the following drawings and description. The components in the figures are not necessarily to scale, with emphasis instead being placed upon illustrating the principles of the invention. Moreover, in the figures, like referenced numerals designate corresponding parts throughout the different views.

FIGS. 5A-5D depict illustrative embodiments of micro-needle 10.

DEFINITIONS

Figure 1A:
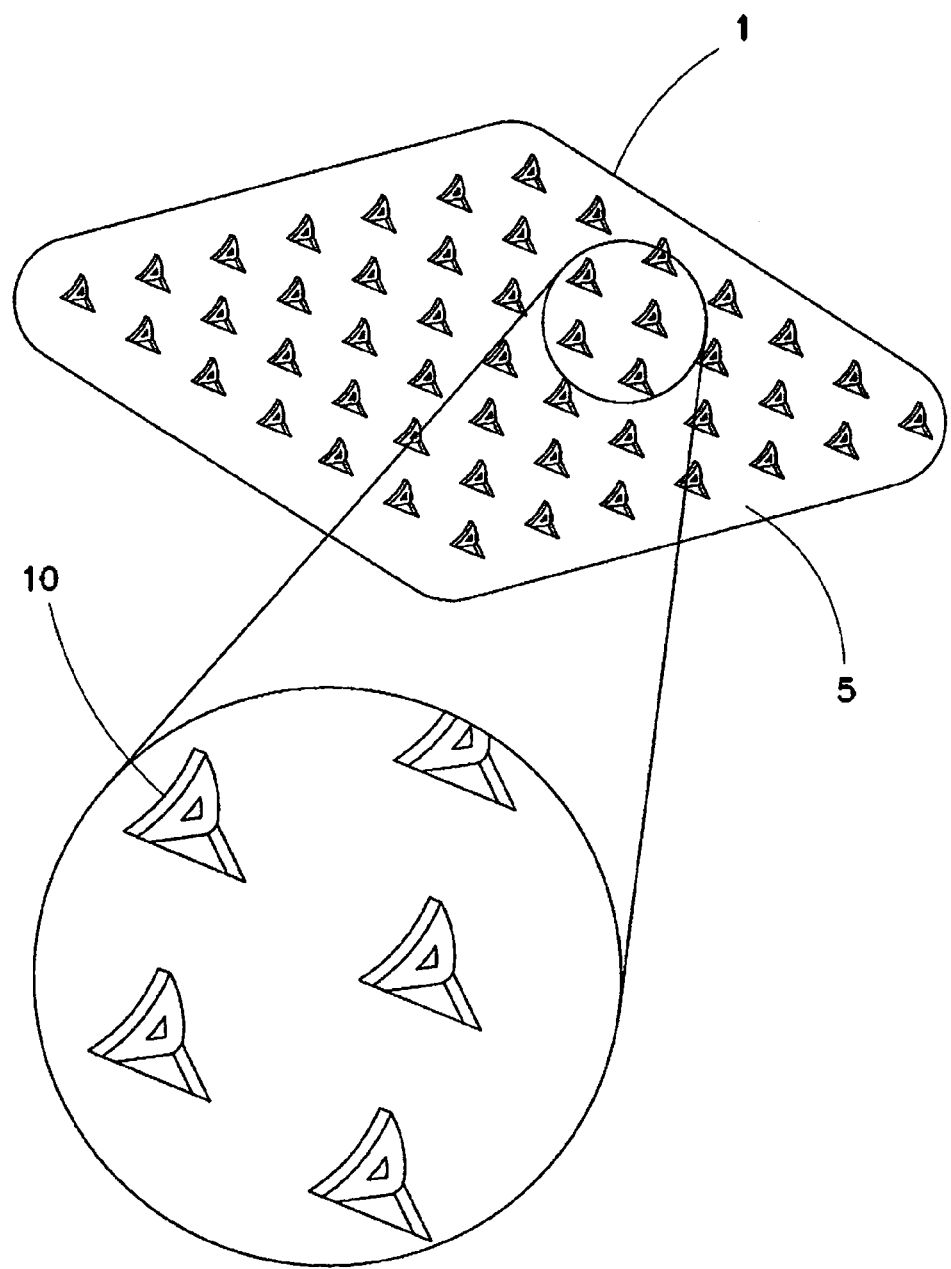
FIGS. 1A-1B depict illustrative embodiments of micro-needle array 1.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

The term "biocompatible," as used herein, refers to a material that is substantially non-toxic in the in vivo environment of its intended use, and that is not substantially rejected by the patient's physiological system. A biocompatible structure or material, when introduced into a majority of patients, will not cause an undesirably adverse, long-lived or escalating biological reaction or response. Such a response is distinguished from a mild, transient inflammation which typically accompanies surgery or implantation of foreign objects into a living organism.

The term "biodegradable," as used herein, refers to a material that dissipates upon implantation within a body, independent of the mechanisms by which dissipation can occur, such as dissolution, degradation, absorption and excretion. The actual choice of which type of materials to use may readily be made by one of ordinary skill in the art. Such materials are often referred to by different terms in the art, such as "bioresorbable," "bioabsorbable," or "biodegradable," depending upon the mechanism by which the material dissipates. The prefix "bio" indicates that the erosion occurs under physiological conditions, as opposed to other erosion processes, caused for example, by high temperature, strong acids or bases, UV light or weather conditions.

The term "controlled release," as used herein, refers to the release of an agent at a predetermined rate. A controlled release may be constant or vary with time. A controlled release may be characterized by a drug elution profile, which shows the measured rate that the agent is removed from a device in a given solvent environment as a function of time. For example, a controlled release elution profile from a medical device may include an initial burst release associated with the deployment of the device, followed by a more gradual subsequent release. A controlled release may be a gradient release in which the concentration of the agent released varies over time or a steady state release in which the agent is released in equal amounts over a certain period of time (with or without an initial burst release).

The term "barrier layer," as used herein, is any layer that is placed over at least a portion of a bioactive agent present in or on a portion of a device of the present invention. In general, the bioactive agent will not be present in the barrier layer. Any mixing of a bioactive agent with the barrier layer is unintentional and merely incidental. The barrier layer may or may not be the outer-most layer present on the device. For example, a bioactive agent may be coated onto a surface of the device, a first barrier layer placed over the bioactive agent and further barrier layers and layers containing the same or a different bioactive agent placed on the first barrier layer. The barrier layer may control the release of the bioactive agent from the device upon implantation.

The term "carrier material," as used herein, refers to a material that forms a mixture with bioactive agent on or in a device of the present disclosure. The carrier material may control the release of the bioactive agent from the device.

The term "bioactive agent," as used herein, refers to any pharmaceutically active agent that produces an intended therapeutic effect on the body to treat or prevent conditions or diseases.

The term "treatment" or "treating," as used herein, describes the management and care of a human or veterinary patient for the purpose of combating or preventing a disease, condition, or disorder and includes the administration of a bioactive agent to alleviate the symptoms or complications, or eliminate the disease, condition, or disorder.

The term "therapeutically-effective amount," as used herein, is the minimal amount of a bioactive agent which is necessary to impart therapeutic benefit to a human or veterinary patient. For example, a "therapeutically effective amount" to a human or veterinary patient is such an amount which induces, ameliorates or otherwise causes an improvement in the pathological symptoms, disease progression or physiological conditions associated with or resistance to succumbing to a disorder, for example restenosis.

DETAILED DESCRIPTION

Figure 1B:
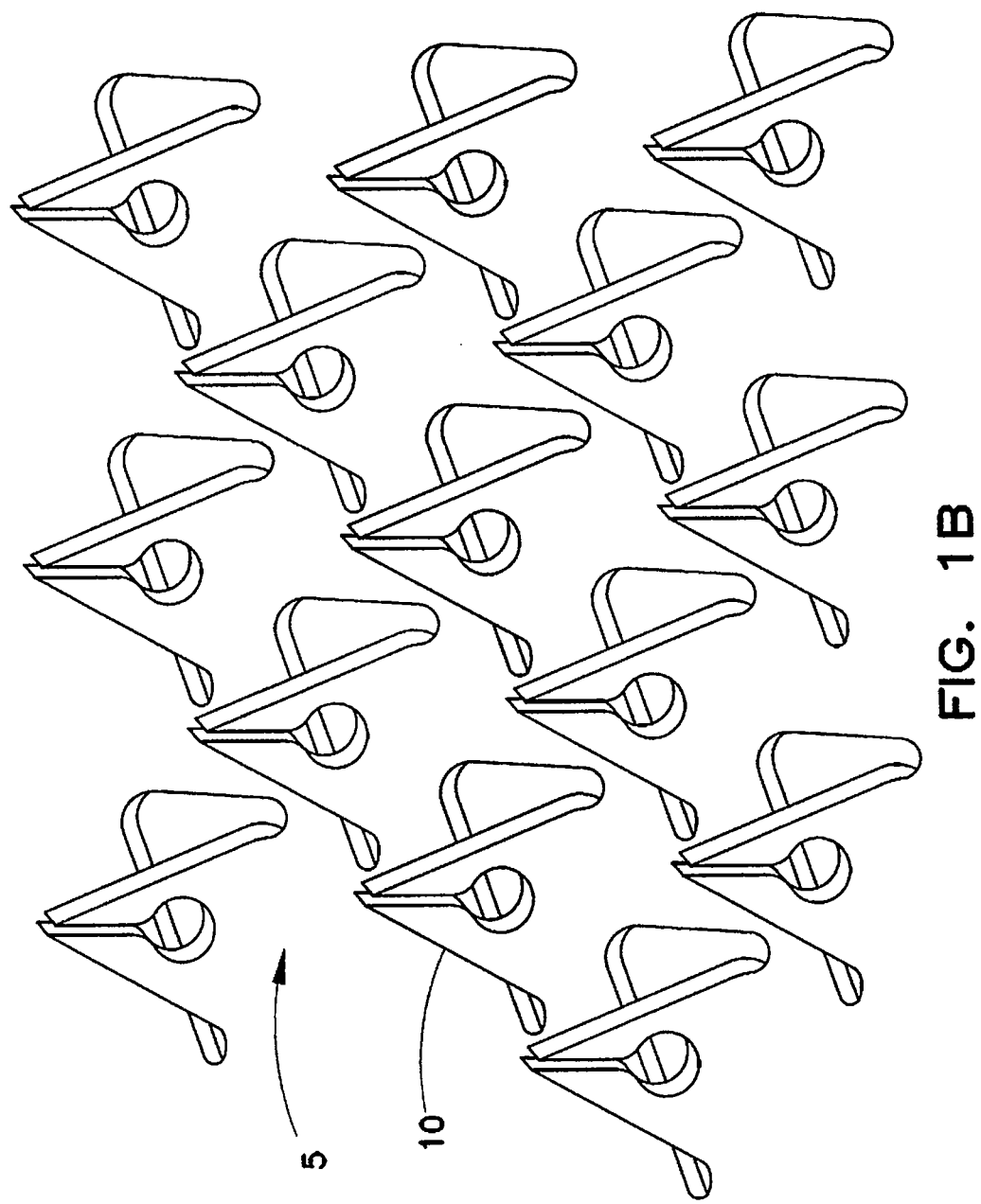

FIGS. 1A-1B depict illustrative embodiments of micro-needle array 1. The array includes a substrate 5 and a plurality of micro-needles 10. The array may include a bioactive agent disposed thereupon. The micro-needle array may be attached to or integrally formed with a device configured for delivery to a therapeutic target. For example, the micro-needle array can be attached to or integrally formed with an inflatable balloon mounted on a catheter shaft. Alternatively, the array may be attached to or integrally formed with an expandable stent. Inflation of the balloon or expansion of the stent preferably causes the micro-needles to contact a layer of tissue at the therapeutic target. Preferably, the micro-needles penetrate at least one layer of tissue of the therapeutic target, delivering bioactive agent thereto.

Figure 2:
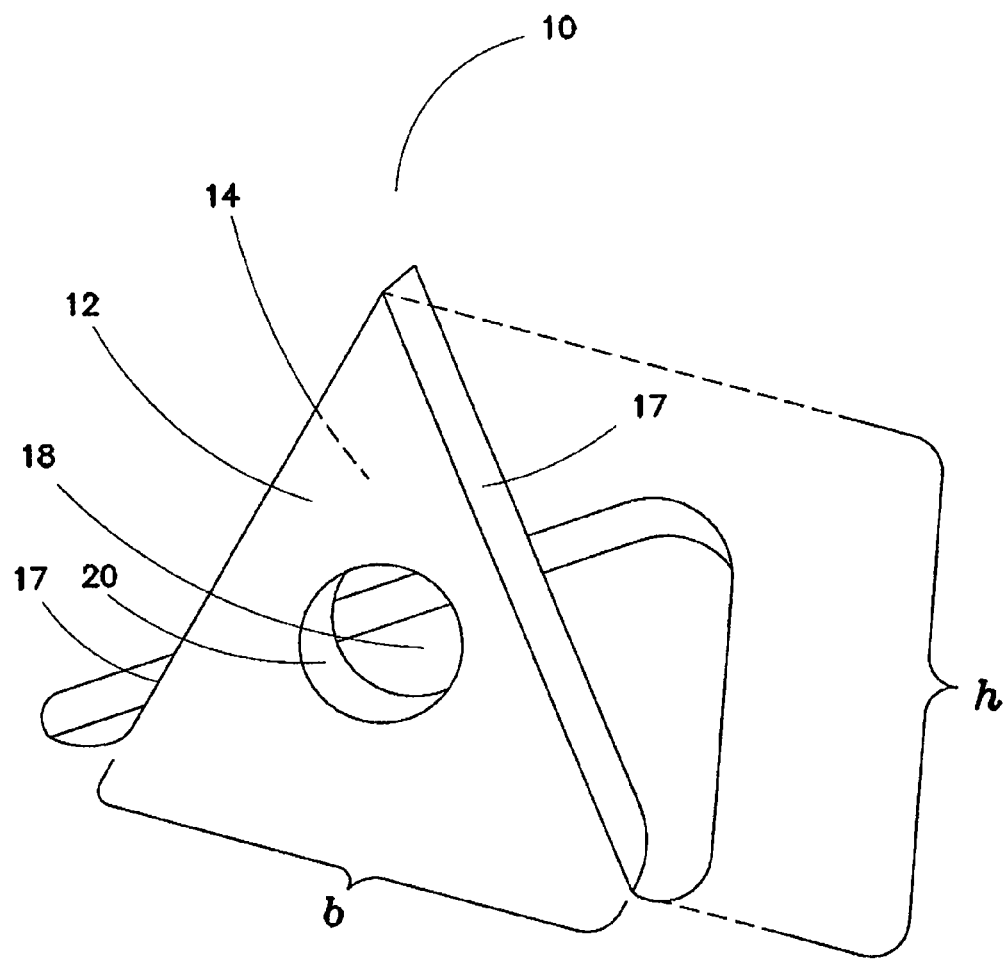
FIG. 2 depicts an illustrative embodiment of micro-needle 10.

FIG. 2 depicts an illustrative embodiment of micro-needle array 1 wherein micro-needle 10 includes a top surface 12, a bottom surface 14, and two side surfaces 17. The side surfaces extend from the top surface 12 to the bottom surface 14. Micro-needle 10 further includes a cavity 18, defined by at least one inner surface 20. Cavity 18 extends from the top surface 12 to the bottom surface 14 (i.e., the cavity has an opening at each of the top surface and the bottom surface). The inner surface(s) of cavity 18 may define a variety of cavity shapes, such as for example, a right circular cylindrical cavity, a triangular cavity, a rectangular cavity, a truncated cylindrical cavity, an obround cavity, an oval cavity, or a pear-shaped cavity. In general, the volume of the cavity ranges from about 4 cubic microns to about 0.140 cubic millimeters, about 10 cubic microns to about 0.100 cubic millimeters, or about 25 cubic microns to about 0.075 cubic millimeters.

As shown in FIG. 2, micro-needle 10 has a base length b and a height h. The base length is the length of the micro-needle at the intersection of the micro-needle with the substrate. The height is the perpendicular distance from the base of the micro-needle to the point of the micro-needle farthest from the base. The height generally ranges from about 10 µm to about 250 µm, preferably about 10 µm to about 100 µm. The base length generally ranges from about 10 µm to about 250 µm, preferably about 10 µm to about 100 µm. Preferably, the ratio of the height to the base length is about 1:1. In some embodiments, the micro-needles may be configured to a height so as to penetrate only the inner-most layer of intima. In other embodiments, micro-needles of the same array may have variable heights such that the micro-needles penetrate different layers of tissue, such as for example, the media or the adventitia. Micro-needle 10, as well as substrate 5, generally has a thickness that ranges from about 1 micron to about 25 microns, preferably about 1 micron to about 10 microns.

Micro-needle array 1 may include a bioactive agent. Preferably, micro-needle 10 includes one or more bioactive agents disposed on one or more of its surfaces. A portion of the bioactive agent may be disposed within cavity 18 and/or on the cavity's inner surface(s). In general, the bioactive agent is delivered to the therapeutic target upon contact with the micro-needles. In some instances, a surrounding body fluid or another fluid may aid in delivery of the bioactive agent to the therapeutic target. For example, upon delivery of the micro-needle array to the therapeutic target, a surrounding body fluid may enter cavity 18 and form a solution, a mixture, a suspension, or an emulsion with the bioactive agent. The fluid and the bioactive agent may be held in the cavity by surface tension until contact with the therapeutic target. Once the micro-needles contact, and preferably penetrate the therapeutic target, the bioactive agent may be delivered thereto.

Figure 3:
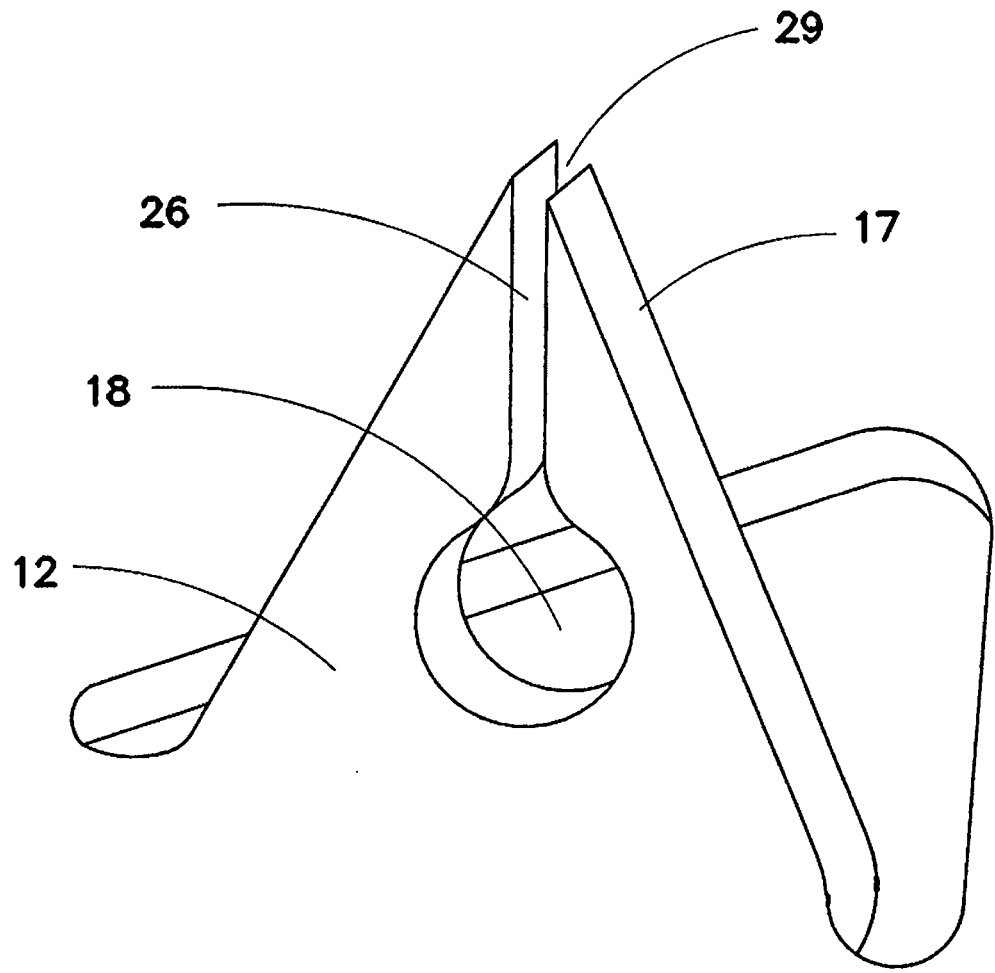
FIG. 3 depicts an illustrative embodiment of micro-needle 10.

FIG. 3 depicts an illustrative embodiment of micro-needle array 1 wherein micro-needle 10 includes a slit 26. The slit extends longitudinally from cavity 18 to an aperture 29 located between two side surfaces. The slit extends from the top surface 12 to the bottom surface 14 (i.e., the slit is open at each of the top surface and the bottom surface). The length of the slit ranges from about 4 microns to about 100 microns, preferably about 4 microns to about 40 microns. The slit provides a path for bioactive agent occupying cavity 18 to move to the target tissue. In some instances, as micro-needle 10 contacts the therapeutic target, the fluid and bioactive agent may move from cavity 18 through slit 26 and to the target. Preferably, the micro-needle penetrates an inner layer of tissue of the therapeutic target and the bioactive agent is delivered thereto.

Figure 4D:
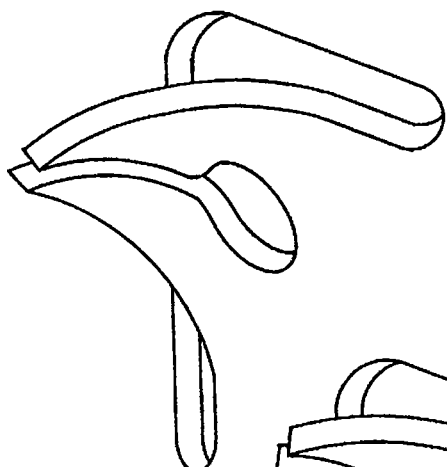
FIGS. 4A-4E depict illustrative embodiments of micro-needle 10.
Figure 4C:
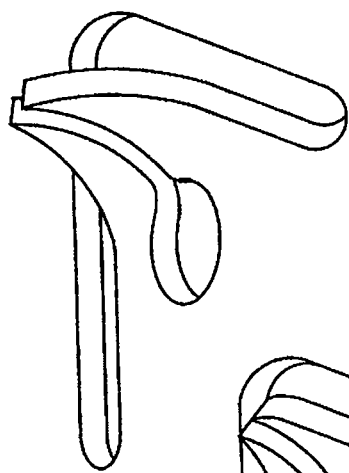
Figure 4B:
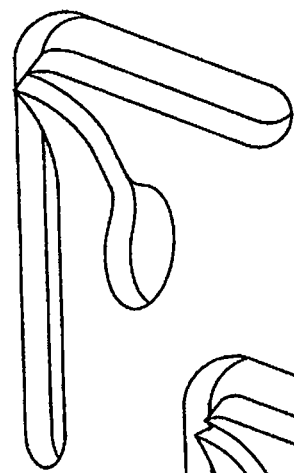
Figure 4A:
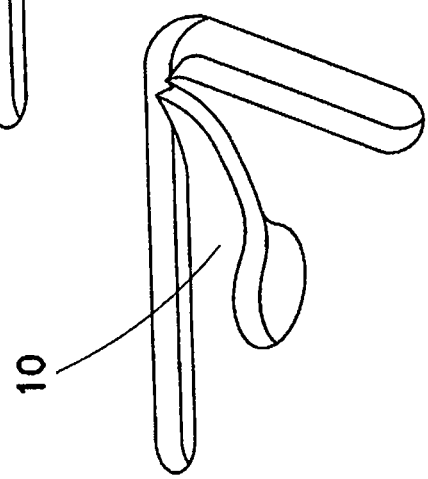
Figure 4E:
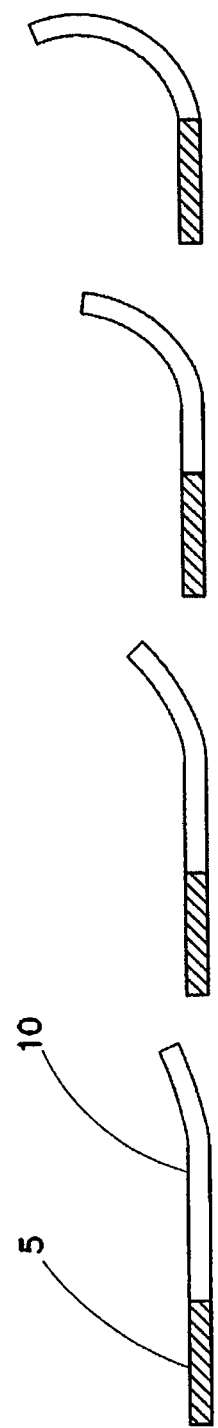

FIGS. 4A-4E depict an illustrative embodiment of micro-needle array 1 wherein the micro-needles have a passive configuration and an active configuration. In the passage configuration, the micro-needles are generally aligned with the substrate. In the active configuration, the micro-needles are generally extending from the substrate. FIG. 4A shows micro-needle 10 in a passive configuration; FIGS. 4B-4C show micro-needle 10 in an intermediate configuration between passive and active; and FIG. 4D shows micro-needle 10 in an active configuration. FIG. 4E shows a side perspective view of micro-needle 10 transitioning from a passive configuration to an active configuration. Where the micro-needle array comprises a shape-memory material, the array may be heat-set such that the micro-needles are in a passive configuration during delivery and thereafter assume an active configuration when activated by a selected temperature, preferably body temperature. With the micro-needles in a passive configuration, the micro-needle array may be more easily introduced to the therapeutic target, and in addition, may diminish the chance of injury to surrounding tissue during introduction.

The micro-needles may be heat-set to assume an active configuration of about perpendicular or greater or less than perpendicular to substrate 5. Transition from a passive configuration to an active configuration may aid in delivery of bioactive agent to the therapeutic target. Specifically, movement of the micro-needle during transition may cause bioactive agent coated on the micro-needle array surfaces to flake, loosen, or break away. In this manner, the bioactive agent may be effectively delivered to the therapeutic target as the micro-needles transition and contact the therapeutic target.

FIGS. 5A-5D depict an illustrative embodiment of micro-needle array 1 wherein slit 26 has a closed configuration and an open configuration. In the closed configuration, the two sides of the slit are in intimate contact with one another, preferably along the entire length of the slit. In the open configuration, the two sides of the slit are not in intimate contact with one another and an open path exists between cavity 18 and aperture 29. FIG. 5A shows slit 26 in a closed configuration; FIGS. 5B-5C show slit 26 in an intermediate configuration between open and closed; and FIG. 5D shows slit 26 in an open configuration. The slit may be in a closed configuration until such time as the micro-needle is activated by a selected temperature, preferably body temperature. As the micro-needle is activated, preferably the two sides of the slit move away from one another, opening up a pathway between cavity 18 and aperture 29.

In general, the micro-needle array is attached to or integrally formed with another device, such as for example, a balloon catheter. The micro-needle array may be attached to another device using, for example, a biocompatible glue, adhesive, or suture. In other embodiments, the micro-needle array may be integral with another device. For example, the micro-needle array may be fabricated from a shape-memory material, such as a nickel-titanium alloy, used to manufacture a stent.

Figure 6:
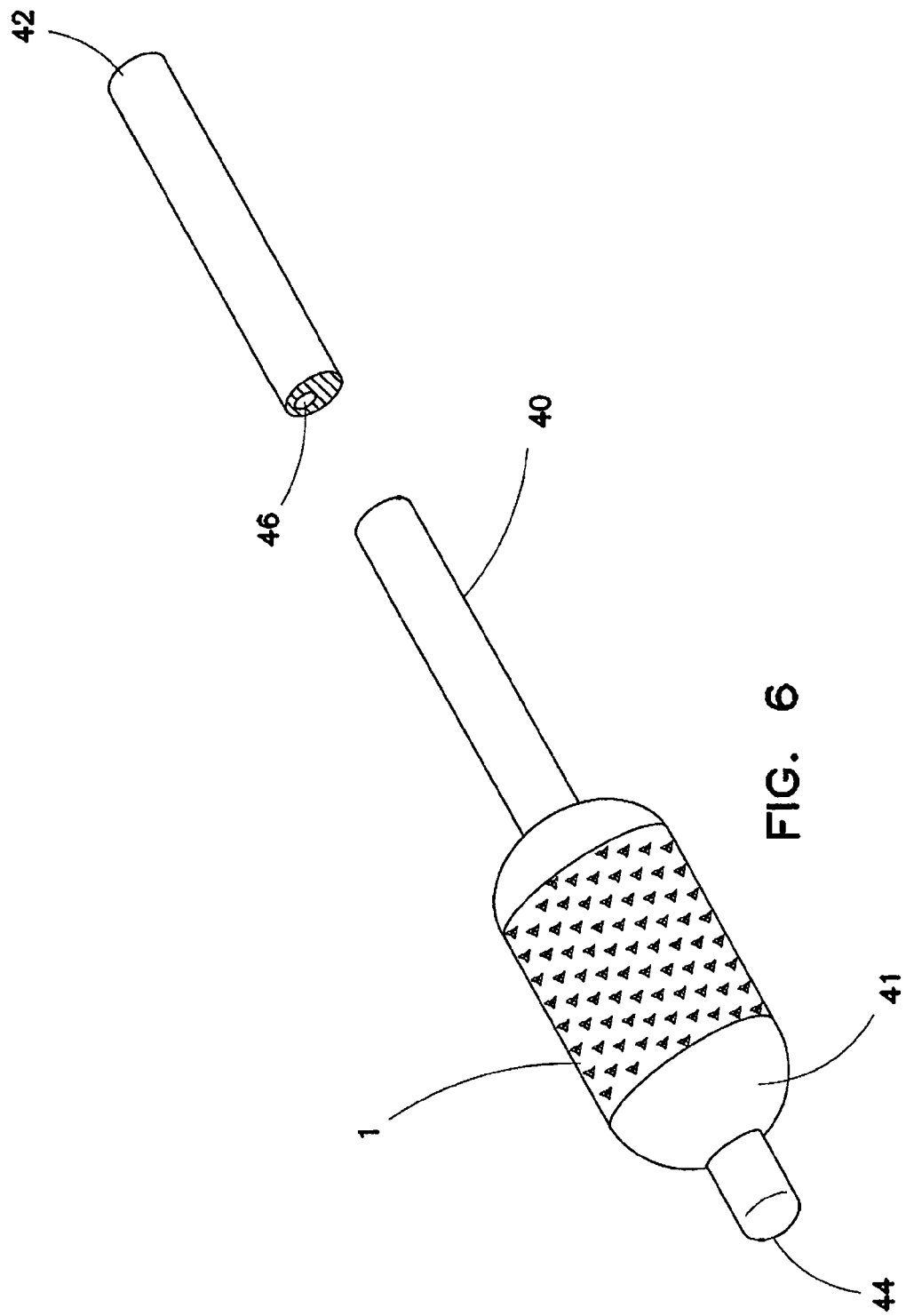
FIG. 6 depicts a balloon catheter with micro-needle array 1 disposed thereon.

FIG. 6 depicts the micro-needle array disposed on an outer surface of a balloon catheter balloon. The balloon catheter includes a catheter shaft 40 extending from a proximal end 42 to a distal end 44 and includes an inflation lumen 46 extending from near the proximal end to near the distal end. A balloon 41 is mounted at the distal end 44 of the shaft. Inflation lumen 46 is in fluid communication with the interior of the balloon. The micro-needle array 1 overlays the outside surface of the balloon and extends from near the distal end of the balloon to near the proximal end of the balloon. Preferably, the micro-needle array overlays the working surface of the balloon. The working surface is that portion of the balloon surface that contacts the vessel wall upon inflation of the balloon.

Figures 7A, 7B:
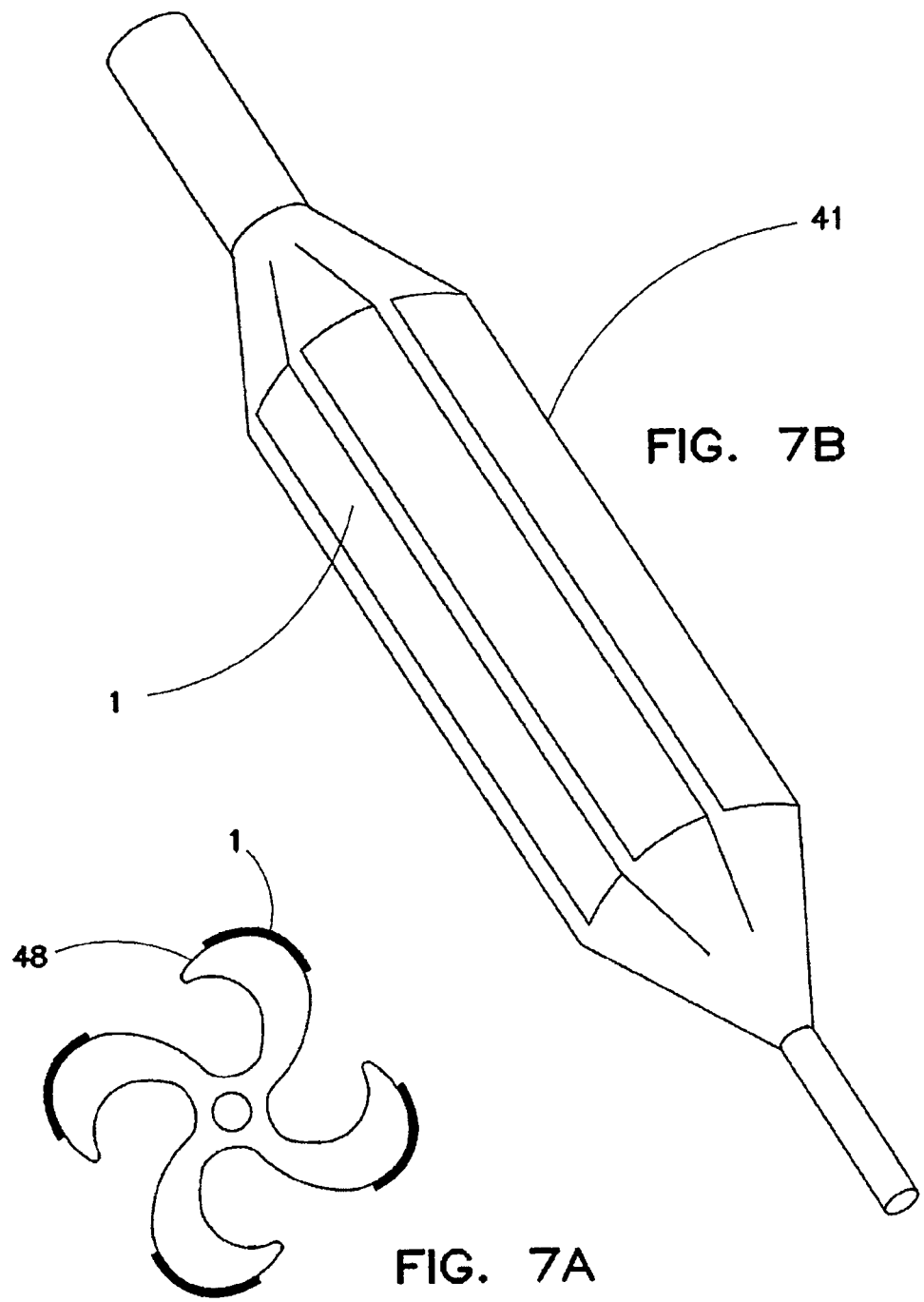
FIGS. 7A-7D depict a balloon catheter with micro-needle arrays 1 disposed thereon.
Figures 7C, 7D:
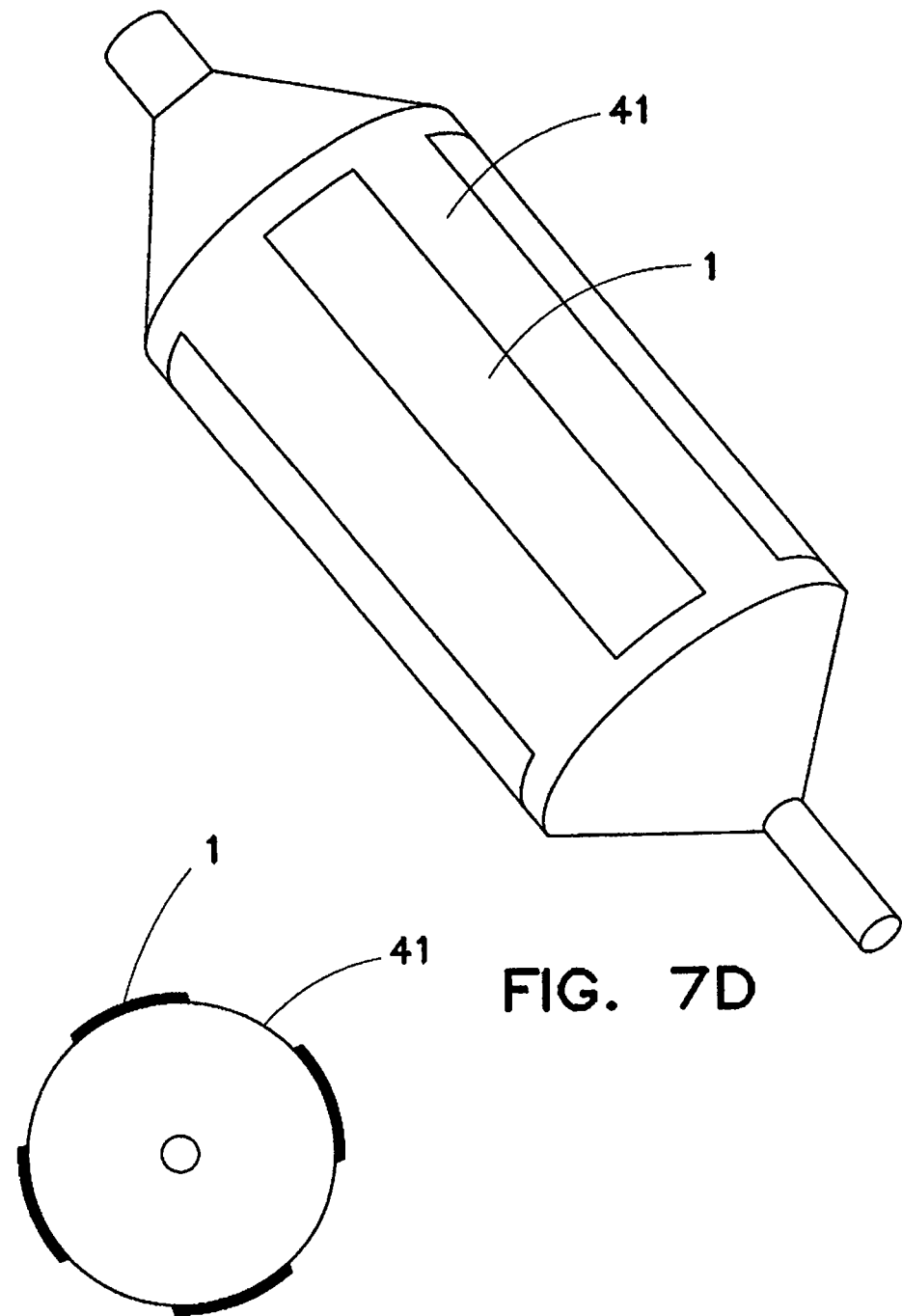

FIGS. 7A-7B depict a spiral-pleat folded balloon 41 having a plurality of micro-needle arrays 1 disposed on its outer surface. FIG. 7A shows an end perspective view of balloon 41 and FIG. 7B shows a top perspective view. The arrays can be arranged on the curved wing surfaces 48 of the pleated balloon surface. The balloon can then be inflated such that the outer surface of the balloon presents a plurality of evenly arranged micro-needle arrays, as shown in FIGS. 7C-7D. FIG. 7C shows an end perspective view of balloon 41 and FIG. 7D shows a top perspective view.

In another aspect, a method is provided for delivering a bioactive agent to a therapeutic target. The method includes delivering the micro-needle array to the therapeutic target followed by contact therewith. Preferably, devices of the present disclosure can be compressed and/or folded or twisted into a delivery configuration. Preferably, the micro-needle array can be delivered to any suitable body vessel, including a vein, artery, biliary duct, ureteral vessel, body passage or portion of the alimentary canal. While the micro-needle array may have particular application in the treatment of stenosis or restenosis, other embodiments provide for delivery to other body vessels.

In some embodiments, the micro-needle array and a device it is disposed upon or contiguous with may be able to navigate small or tortuous paths through a variety of body vessels, particularly where the devices are capable of a compressed delivery configuration having great flexibility with a very low profile and a small collapsed diameter. A low-profile device may also be useful in coronary arteries, carotid arteries, vascular aneurysms, and peripheral arteries and veins (e.g., renal, iliac, femoral, popliteal, sublavian, aorta, intercranial, etc.). Other nonvascular applications include gastrointestinal, duodenum, biliary ducts, esophagus, urethra, reproductive tracts, trachea, and respiratory (e.g., bronchial) ducts.

In certain embodiments, the micro-needle array is used to treat a narrowing of a peripheral artery or vein. Examples of such arteries include, but are not limited to, the femoral artery, the superficial femoral artery (artery below the branch for the profunda femoris artery), the popliteal artery and the infrapopliteal artery. Examples of such veins include, but are not limited to, the femoral vein, the popliteal vein and the lesser/greater saphenous vein. Another application of the array is to open up arteriovenous fistulas that have occluded due to thrombus formation. When used to treat thrombosis, the micro-needle array can deliver an anti-coagulant.

In some embodiments, the devices can be compressed to a delivery configuration within a retaining sheath that is part of a delivery system. Where the micro-needle array is disposed on a balloon catheter, the balloon can be expanded by removing the sheath followed by inflation of the balloon. The delivery configuration can be maintained prior to deployment of the device by any suitable means, including a sheath, a suture, a tube or other restraining material around all or part of the device.

The devices may be deployed according to well-known deployment techniques for expandable medical devices. For example, the micro-needle array can be positioned at the distal end of a balloon catheter with a lubricous sleeve placed over the array and the balloon to hold the medical device in a contracted state with a relatively small diameter. The array may then be delivered to the point of treatment by advancing the catheter over a guidewire to the therapeutic target and then withdrawing the sleeve from over the device. The balloon may then be expanded to bring the micro-needle array, the micro-needles in particular, into contact with the therapeutic target.

Expansion of the balloon preferably results in a therapeutically-effective amount of a bioactive agent being delivered to the therapeutic target, typically a vessel wall. The bioactive agent may be delivered from the balloon outer surface and/or the micro-needle array. The bioactive agent may be delivered by a controlled release of the bioactive agent. In various embodiments, at least 90 percent of the bioactive present on the array or on or within the material of the balloon catheter is released into an aqueous physiological environment within 30 sec, 1 minute, 2 minutes, 5 minutes, 10 minutes, 15 minutes, 20 minutes, 30 minutes, 45 minutes, 60 minutes or 90 minutes.

The micro-needle array may be fabricated by conventional techniques known to those skilled in the art. Preferably, the micro-needles are fabricated from the same material as substrate 5 such that the micro-needles are integrally formed with the substrate. The array may be fabricated using a rapid prototyping technique, such as stereolithography, lamininated object manufacturing, selective laser sintering, fused deposition modeling, CNC laser-cutting, and 3-D printing. The array can be fabricated to any shape or dimensions suitable for the intended use. In addition, the micro-needles can be fabricated to any shape suitable for the intended use. For example, the micro-needles may be fabricated into triangular shaped micro-needles (as depicted in FIGS. 1-7), rectangular shaped micro-needles, or semi-circular shaped micro-needles. The micro-needles generally have a distribution on the substrate of greater than about ten micro-needles per $cm^2$, preferably between about $1 \times 10^2$ and about $1 \times 10^6$ per $cm^2$, more preferably between about $1 \times 10^3$ and about $1 \times 10^5$ $cm^2$. In some embodiments, the micro-needle array may include several layers of material. In particular, substrate 5, including the micro-needles, may overlay one or more additional layers of material.

In a preferred embodiment, the micro-needle array is fabricated using CNC laser-cutting. A CNC controlled laser may be used to cut the micro-needle pattern from a metallic substrate. Heat may then be applied to a surface of the substrate, causing the cut micro-needles to curl up to the heat applied surface in a controlled manner. After the micro-needles are curled into position, the array may undergo further fabrication procedures. For example, the array may be trimmed to preferred dimensions and thereafter affixed to an underlying device. In some embodiments, the micro-needles may be forced back into a passive configuration, whereupon the micro-needles can redeploy to an active configuration when activated by a selected temperature change.

The micro-needle array may be fabricated from a variety of biocompatible materials, including metals and polymeric materials. Suitable metals or metal alloys include stainless steels, nickel-titanium alloys including shape memory or superelastic types; inconel; noble metals including copper, silver, gold, platinum, palladium and iridium; refractory metals including molybdenum, tungsten, tantalum, rhenium, or niobium; stainless steels alloyed with noble and/or refractory metals; magnesium; amorphous metals; plastically deformable metals; nickel-based alloys; iron-based alloys; cobalt-based alloys; cobalt-chrome alloys; cobalt-chromium-nickel alloys; alloys of cobalt, nickel, chromium and molybdenum; cobalt-chromium-vanadium alloys; cobalt-chromium-tungsten alloys; platinum-iridium alloys; platinum-tungsten alloys; magnesium alloys; titanium alloys; tantalum alloys; L605; magnetic ferrite, bioabsorbable materials, including magnesium; or other biocompatible metals and/or alloys thereof. One particularly preferred material is a self-expanding material such as the superelastic nickel-titanium alloy sold under the tradename NITINOL.

Other suitable materials include carbon or carbon fiber, cellulose acetate, cellulose nitrate, silicone, polyethylene terephthalate, polyurethane, polyamide, polyester, polyorthoester, polyanhydride, polyether sulfone, polyanhydride, polycarbonate, polypropylene, high molecular weight polyethylene, polylactic acid, polyglycolic acid, polytetrafluoroethylene, polycaprolactone, polyhydroxybutyrate valerate, a biodegradable polymer, or another biocompatible polymeric material, or mixtures or copolymers thereof. In one embodiment, the micro-needle array may be cast from a thermoset polymer, or micro-molded from a thermoplastic polymer. A female mold can be used to produce a micro-needle array as described herein. Preferred polymers include, but are not limited to, polyetheretherketones, polyurethane, polyethylene terephthalate, Pebax, and nylon.

One or more bioactive agents may be applied to the micro-needle array. A bioactive agent may be applied directly on the surface of the micro-needle array (or on a primer layer, which is placed directly on the surface of the micro-needle array). Alternatively, the bioactive agent may be mixed with a carrier material and this mixture applied to the array. In such configuration, the release of the bioactive agent may be dependent on factors including composition, structure and thickness of the carrier material. The carrier material may contain pre-existing channels, through which the bioactive agent may diffuse, or channels created by the release of bioactive agent, or another soluble substance, from the carrier material.

One or more barrier layers may be deposited over the layer containing the bioactive agent. A combination of one or more layers of bioactive agent, mixtures of carrier material/bioactive, and barrier layers may be present. The bioactive agent may be mixed with a carrier material and coated onto the array and then over coated with barrier layer(s). Multiple layers of bioactive agent, or mixtures of carrier material/bioactive, separated by barrier layers may be present to form a multicoated micro-needle array. Different bioactive agents may be present in the different layers.

The carrier material and/or the barrier layer can include a bioelastomer, PLGA, PLA, PEG, Zein, or a hydrogel. In certain other embodiments, the carrier material and/or the barrier layer includes microcrystalline cellulose, hydroxypropylmethyl cellulose, hydroxypropyl cellulose, a cellulose product, a cellulose derivative, a polysaccharide or a polysaccharide derivative. The carrier material and/or barrier layer may include lactose, dextrose, mannitol, a derivative of lactose, dextrose, mannitol, starch or a starch derivative. The carrier material and/or barrier layer may include a biostable or a biodegradable material, for example, a biostable or biodegradable polymer.

Where the bioactive agent is coated onto the micro-needle array, it may be advantageous to prepare the surface of the array before depositing a coating thereon. Useful methods of surface preparation can include, but are not limited to cleaning; physical modifications such as etching, drilling, cutting, or abrasion; and chemical modifications such as solvent treatment, the application of primer coatings, the application of surfactants, plasma treatment, ion bombardment, covalent bonding and electrochemical methods such as electropolishing, striking, electroplating and electrochemical deposition. Such surface preparation may serve to activate the surface and promote the deposition or adhesion of the coating on the surface. Surface preparation can also selectively alter the release rate of the bioactive.

Any additional coating layers can similarly be processed to promote the deposition or adhesion of another layer, to further control the release of the bioactive agent, or to otherwise improve the biocompatibility of the surface of the layers. For example, plasma treating an additional coating layer before depositing a bioactive agent thereon may improve the adhesion of the bioactive agent, increase the amount of bioactive agent that can be deposited, and allow the bioactive agent to be deposited in a more uniform manner.

A primer layer, or adhesion promotion layer, may also be applied to the micro-needle array. This layer may comprise, for example, silane, acrylate polymer/copolymer, acrylate carboxyl and/or hydroxyl copolymer, polyvinylpyrrolidone/vinylacetate copolymer (PVP/VA), olefin acrylic acid copolymer, ethylene acrylic acid copolymer, epoxy polymer, polyethylene glycol, polyethylene oxide, polyvinylpyridine copolymers, polyamide polymers/copolymers polyimide polymers/copolymers, ethylene vinylacetate copolymer and/or polyether sulfones.

The bioactive agent may be applied, for example, by spraying, dipping, pouring, pumping, brushing, wiping, vacuum deposition, vapor deposition, plasma deposition, electrostatic deposition, ultrasonic deposition, epitaxial growth, electrochemical deposition or any other method known to the skilled artisan. The bioactive agent may be applied as a separate layer or may be included in a layer also including a carrier material.

A variety of bioactive agents may be applied to the micro-needle array in accordance with the intended use. For example, antithrombogenic agents may be applied to the array. An antithrombogenic agent is any agent that inhibits or prevents thrombus formation within a body vessel. Types of antithrombotic agents include anticoagulants, antiplatelets, and fibrinolytics. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic agents include anticoagulants such as heparin, low molecular weight heparin, covalent heparin, synthetic heparin salts, coumadin, bivalirudin(hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Other bioactive agents that may be applied include antiproliferative/antimitotic agents including natural products such as vinca alkaloids(vinblastine, vincristine, and vinorelbine), paclitaxel, rapamycin analogs, epidipodophyllotoxins (etoposide, teniposide), antibiotics(dactinomycin(actinomycin D)daunorubicin, doxorubicin and idarubicin), anthracyclines, mitoxantrone, bleomycins, plicamycin(mithramycin) and mitomycin, enzymes (for example, L-asparaginase which systemically metabolizes L-asparagine and deprives cells which do not have the capacity to synthesize their own asparagine); antiplatelet agents such as (GP) IIb/IIIa inhibitors and vitronectin receptor antagonists; antiproliferative/antimitotic alkylating agents such as nitrogen mustards(mechlorethamine, cyclophosphamide and analogs, melphalan, chlorambucil), ethylenimines and methylmelamines(hexamethylmelamine and thiotepa), alkyl sulfonates-busulfan, nirtosoureas(carmustine (BCNU) and analogs, streptozocin), trazenes-dacarbazinine (DTIC); antiproliferative/antimitotic antimetabolites such as folic acid analogs(methotrexate), pyrimidine analogs(fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants(heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory(breveldin); anti-inflammatory: such as adrenocortical steroids(cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus(rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; antisense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin;

pimecrolimus; angiopeptin; HMG co-enzyme reductase inhibitors (statins); metalloproteinase inhibitors (batimastat); protease inhibitors; antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat.

In a preferred embodiment, the bioactive agent applied to the micro-needle array is selected from the group consisting of paclitaxel, rapamycin, a rapamycin derivative, an antisense oligonucleotide, and a mTOR inhibitor.

While various embodiments of the micro-needle array have been described, it will be apparent to those of ordinary skill in the art that many more embodiments and implementations are possible within the scope of the invention. Accordingly, the invention is not to be restricted except in light of the attached claims and their equivalents.

I claim:

1. A micro-needle array comprising:
   a substrate;
   a plurality of micro-needles integral with the substrate, wherein at least one micro-needle comprises a body comprising:
      a top surface,
      a bottom surface,
      a side surface extending from the top surface to the bottom surface, and
      a cavity within the body and defined by an inner surface, the cavity extending from the top surface to the bottom surface; and
   a bioactive agent disposed on the substrate and the plurality of micro-needles,
   wherein the at least one micro-needle further comprises a slit connecting the cavity to an aperture on the side surface, the slit extending from the top surface to the bottom surface,
   wherein the slit has a closed configuration and an open configuration.

2. The micro-needle array of claim 1 wherein the cavity has a volume of about 4 cubic microns to about 0.140 cubic millimeters.

3. The micro-needle array of claim 1 wherein the at least one micro-needle has a base length of about 10 µm to about 250 µm and a height of about 10 µm to about 250 µm.

4. The micro-needle array of claim 1 wherein the at least one micro-needle has a passive configuration in which the at least one micro-needle is generally aligned with the substrate and an active configuration in which the at least one micro-needle is generally extending from the substrate.

5. The micro-needle array of claim 1 wherein the at least one micro-needle comprises a material selected from the group consisting of stainless steel alloys and nickel-titanium alloys.

6. The micro-needle array of claim 1 wherein the micro-needle array is disposed on or integrally formed with one of a balloon catheter or a stent.

7. The micro-needle array of claim 1 wherein the bioactive agent is selected from the group consisting of paclitaxel, rapamycin, a rapamycin derivative, an antisense oligonucleotide, and a mTOR inhibitor.

8. The micro-needle array of claim 1 wherein the micro-needle array is fabricated using a process selected from the group consisting of stereolithography, lamininated object manufacturing, selective laser sintering, fused deposition modeling, CNC laser-cutting, and 3-D printing.

9. The micro-needle array of claim 1 wherein the at least one micro-needle has a base length of about 10 µm to about 250 µm and a height of about 10 µm to about 250 µm, wherein the cavity defines a volume of about 4 cubic microns to about 0.140 cubic millimeters, wherein said micro-needle has a passive configuration in which the at least one micro-needle is generally aligned with the substrate and an active configuration in which the at least one micro-needle is generally extending from the substrate, and wherein said micro-needle comprises a material selected from the group consisting of stainless steel alloys and nickel-titanium alloys.

10. The micro-needle array of claim 9 wherein the at least one micro-needle comprises a slit connecting the cavity to an aperture on the side surface, the slit extending from the top surface to the bottom surface.

11. A micro-needle array comprising:
    a substrate;
    a plurality of micro-needles integral with the substrate, wherein at least one micro-needle comprises a body comprising:
       a top surface,
       a bottom surface,
       a side surface extending from the top surface to the bottom surface, and
       a cavity within the body and defined by an inner surface, the cavity extending from the top surface to the bottom surface; and
    a bioactive agent disposed on the substrate and the plurality of micro-needles,
    wherein the at least one micro-needle has a base length of about 10 µm to about 250 µm and a height of about 10 µm to about 250 µm, wherein the cavity defines a volume of about 4 cubic microns to about 0.140 cubic millimeters, wherein said micro-needle has a passive configuration and an active configuration, and wherein said micro-needle comprises a material selected from the group consisting of stainless steel alloys and nickel-titanium alloys,
    wherein the at least one micro-needle comprises a slit connecting the cavity to an aperture on the side surface, the slit extending from the top surface to the bottom surface,
    wherein the slit has a closed configuration and an open configuration.

* * * * *